United States Patent
Sapian

[19]

[11] Patent Number: 5,890,902
[45] Date of Patent: Apr. 6, 1999

[54] IMPLANT BONE LOCKING MECHANISM AND ARTIFICIAL PERIODONTAL LIGAMENT SYSTEM

[76] Inventor: Schubert L. Sapian, P.O. Box 1922, Loma Linda, Calif. 92354

[21] Appl. No.: 934,498

[22] Filed: Sep. 19, 1997

[51] Int. Cl.[6] .................................................. A61C 8/00
[52] U.S. Cl. ......................... 433/173; 433/174; 433/177
[58] Field of Search ..................... 433/172, 173, 433/174, 175, 176, 177

[56] References Cited

U.S. PATENT DOCUMENTS

| | | | |
|---|---|---|---|
| 4,552,532 | 11/1985 | Mozary | 433/174 X |
| 4,993,950 | 2/1991 | Menser, Jr. | 433/174 |
| 5,049,073 | 9/1991 | Lauks | 433/171 X |
| 5,071,351 | 12/1991 | Green, Jr. et al. | 433/174 X |
| 5,417,570 | 5/1995 | Zuest et al. | 433/177 |
| 5,453,007 | 9/1995 | Wagher | 433/177 |
| 5,779,481 | 7/1998 | Aires | 433/177 X |

*Primary Examiner*—Nicholas D. Lucchesi
*Attorney, Agent, or Firm*—Moreland C. Fischer

[57] ABSTRACT

An implant bone locking mechanism and artificial periodontal ligament system having a hollow implant casing and a set of stabilizing locking pins that are initially retracted within the casing. A pin activator is moved axially through the hollow implant casing to cause the locking pins to move outwardly therefrom and bore into the patient's bone structure in which the implant casing is located to enable immediate bone implant and increase bone/implant stabilization. A locking basket has a pair of outstretched arms and a plurality of locking splines that are coupled to the pin activator and the implant casing to prevent a rotation of the pin activator and implant casing relative to the locking basket and each other. An irremovable crown is seated upon the locking basket and adapted for both lateral movement along the outstretched arms of the locking basket and up and down movement relative to the locking basket so as to function like a natural tooth and improve the quality of mastication.

20 Claims, 5 Drawing Sheets

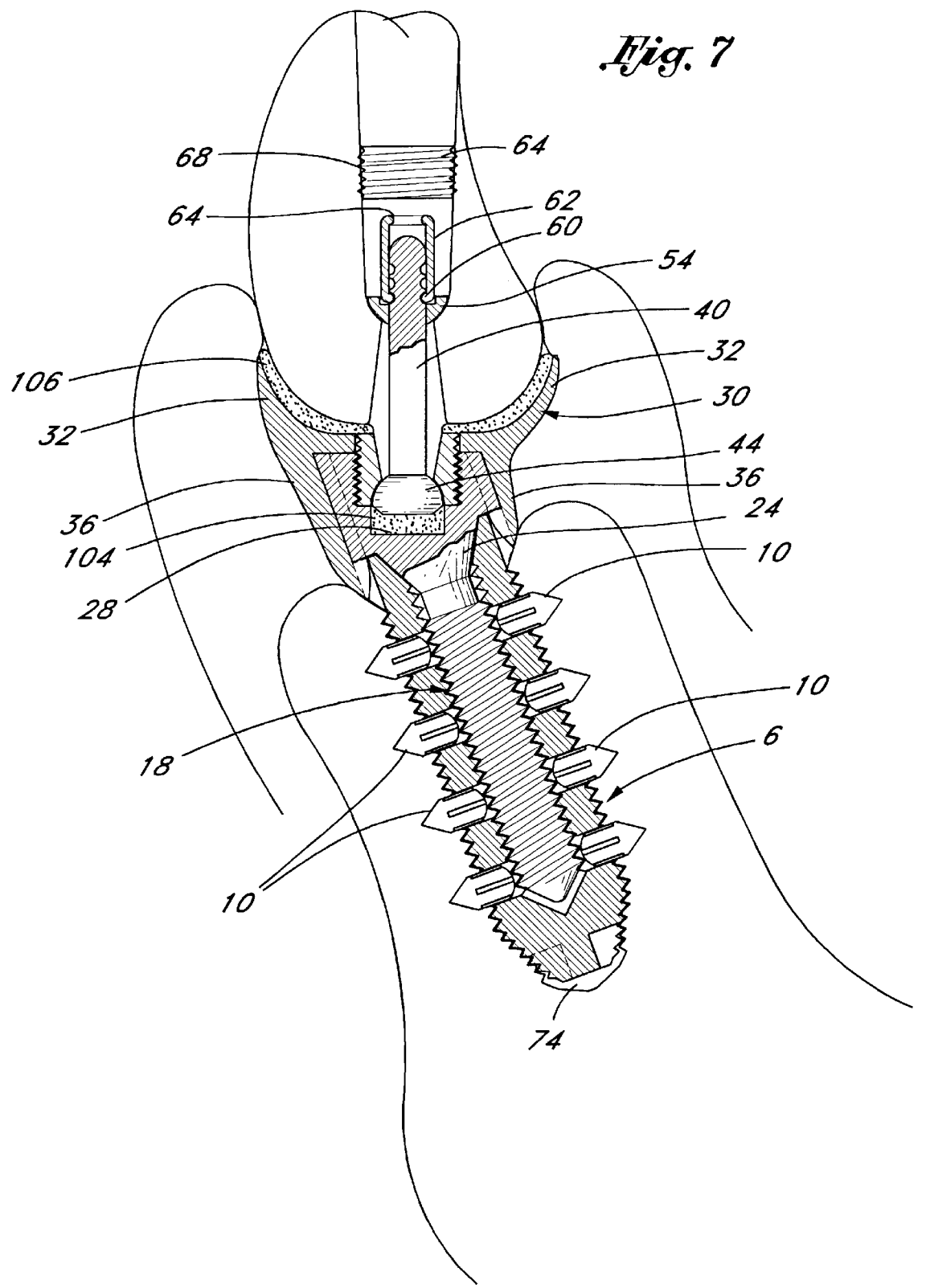

IMPLANT BONE LOCKING MECHANISM AND ARTIFICIAL PERIODONTAL LIGAMENT SYSTEM

BACKGROUND OF THE INVENTION

1. Field of the Invention

This invention relates to an implant bone locking mechanism and artificial periodontal ligament system having a set of locking pins to bore into the patient's bone structure to enable immediate bone implant, increase bone/implant stabilization and provide an avenue to evenly release human growth factors to the bone. The system also has an undetachable crown that is adapted to move laterally as well as up and down to function like a natural tooth.

2. Background Art

Natural teeth in the human mouth are supported in bone by periodontal fibers that function as shock absorbers when a compressive force is applied, such as during chewing. Through disease, accidental injury, anatomical abnormalities, age, and the like, a natural tooth may be removed or missing such that a dental appliance or prosthetic device (e.g. a crown) is implanted in the patient's bone structure to improve the patient's physical appearance and/or quality of mastication. However, conventional implants are often too rigid to function like natural teeth. Problems such as crown breakage, screw loosening and screw breakage are inherent problems with a rigid crown implant. Failure is also known to occur when an implant is used in a bridge abutment with a natural tooth or when improper occlusion is created by the implant crown.

More particularly, screws associated with conventional crowns sometimes break because of over tightening and due to tension and lateral stress to which the crown is subjected during use. Moreover, a single crown can rotate in response to high lateral and torquing forces encountered while chewing, whereby to rotate and loosen screws. As dental professionals will understand, it is difficult and time consuming to retrieve and/or repair such broken screws. In addition, special purpose torque drivers are required to install the screws. Once the crown is implanted, it may take several months to achieve suitable bone integration of the root portion with the surrounding bone structure thereby resulting in increased loading time before the root portion can be reliably anchored. What is still more, many crowns are not adapted to move under loading conditions and, consequently, they cannot easily absorb and distribute shock and other physical forces that are generated during chewing. Such crowns may be susceptible to damage or reduced life and may be unable to provide the function of a natural tooth and the quality of mastication associated therewith.

Accordingly, it would be desirable to overcome the problems associated with conventional crowns by avoiding screws which can break or loosen and the special purpose tools that are needed to install such screws. It would also be desirable to decrease integration time by increasing stabilization between the root portion of the implant and the bone structure of the patient and by promoting tissue growth around the root portion to help anchor the root portion in place and thereby avoid damage to the surrounding bone structure. It would be further desirable that the crown be capable of sliding from side-to-side and moving up and down during chewing so as to emulate a natural tooth. Therefore, patient comfort will be enhanced, the life of the crown will be increased, and the need to make repairs (along with the follow-up visits and corresponding cost) can be reduced.

Examples of known dental implant attachment systems are available by referring to one or more of the following United States patents:

| | | |
|---|---|---|
| 4,756,689 | Lundgren | July 12, 1988 |
| 5,015,186 | Detsch | May 14, 1991 |
| 5,429,505 | Fortin | July 4, 1995 |

SUMMARY OF THE INVENTION

An implant bone locking mechanism and artificial periodontal ligament system is disclosed having a root portion located below the patient's gum line and anchored to the patient's bone structure and a crown portion coupled to the root portion. A crown is irremovably connected to the crown portion and adapted for both lateral and up and down movements relative thereto. The root portion includes a cylindrical implant casing having an implant head at one end and a hollow body at the opposite end with sets of screw threads extending along the exterior and interior thereof. A plurality of sharp locking pins are initially carried at the interior of the implant casing, and a tissue growth factor is injected into the interior of the implant casing. After an area of the patient's gum is removed and a hole is drilled into the patient's bone, the implant casing is rotated into the hole. The external threads of the implant casing are characterized by an occlusal bevel to bite into the surrounding bone structure and increase stabilization.

A pin activator has an abutment head at one end and a threaded abutment stem that terminates with a round point at the opposite end. The pin activator is advanced axially through the interior of the implant casing such that the threaded abutment stem is mated to the screw threads at the interior of the casing. As the abutment stem moves through the interior of the implant casing, the locking pins are partially ejected therefrom so as to bore into the patient's bone structure and anchor the root portion in place so as to avoid micromovements thereof until bone remodeling occurs. Moreover, a human growth factor is expulsed from the implant casing via open windows in the locking pins to be uniformly distributed to the surrounding bone structure.

The crown portion of the implant bone locking mechanism and artificial periodontal ligament system includes a locking basket having a pair of outstretched arms and downwardly projecting locking splines that are surrounded by a cylindrical skirt. In the assembled configuration, the crown is seated upon the wings of the locking basket while the splines of the locking basket are coupled to the implant head of the implant casing and to the abutment head of the pin activator to prevent a rotation of the implant casing and pin activator relative to one another. A swivel rod is received through a central opening of the locking basket so as to extend between the abutment head of the pin activator and an axial cavity formed in the crown. The swivel rod has a series of adjustment grooves extending around one end and a ball swivel formed at the opposite end. The ball swivel is captured and held within the abutment head of the pin activator to form a first pivot point. A swivel rod connector surrounds the swivel rod below the adjustment grooves thereof to form a second pivot point. By locating a snap ring within and a locking tube around one of the adjustment grooves, an adjustable compressive force is applied to the swivel rod connector so as to irremovably connect the crown to the abutment head of the pin activator.

By virtue of the two pivot points created by the ball swivel and the swivel rod connector at opposite ends of the swivel rod, the crown is adapted to slide from side-to-side along the wings of the locking basket and move up and down relative to the abutment head. Accordingly, the forces applied to the crown during chewing will be better absorbed, whereby the crown more closely emulates the movement and function of a natural tooth.

BRIEF DESCRIPTION OF THE DRAWINGS

FIGS. 6 and 7 show a crown irremovably connected to the implant bone locking mechanism and artificial periodontal ligament system, whereby the crown is adapted for both lateral and up and down movements.

DETAILED DESCRIPTION

Figure 1:
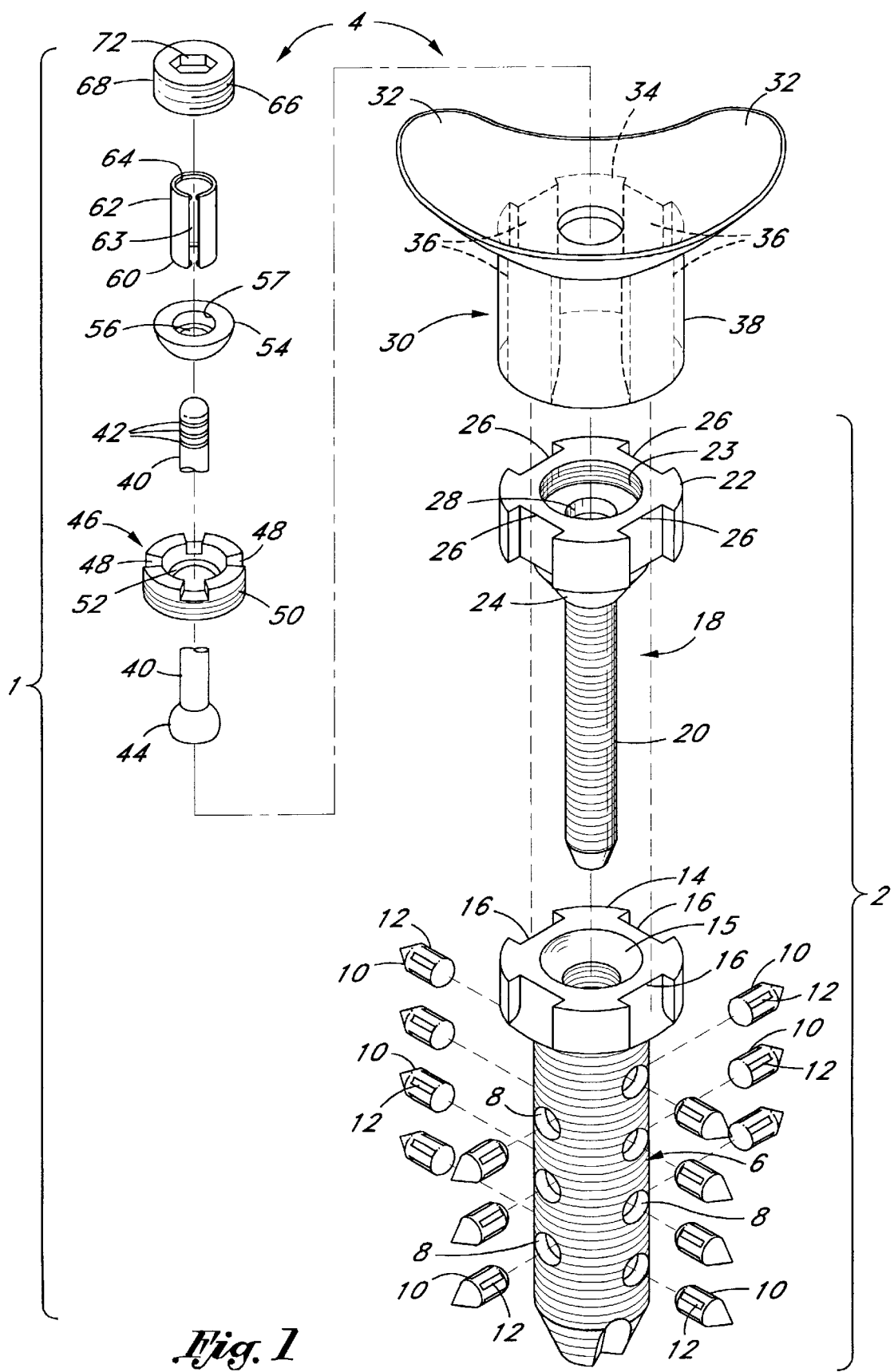
FIG. 1 is an exploded view of the implant bone locking mechanism and artificial periodontal ligament system which forms the present invention.

Referring initially to FIG. 1 of the drawings, there is shown an exploded view of the implant bone locking mechanism and artificial periodontal ligament system 1 which forms the present invention and which includes a root portion 2 and a crown portion 4. As will be described in greater detail hereinafter, when the locking mechanism and ligament system 1 is assembled and implanted, the root portion 2 will lie below the gum line of the patient. The root portion 2 includes a hollow, elongated endosseous implant casing 6 that is preferably manufactured from metal (e.g. titanium or a titanium alloy) so as to avoid galvanic corrosion and provide a medium for osseointegration. The implant casing 6 is shown having a cylindrical body, the exterior of which is threaded with an occlusal bevel and the bottom of which tappers inwardly to enable the implant casing 6 to be firmly implanted and locked within a hole that is to be drilled through the patient's bone (best shown in FIGS. 2 and 3). The implant casing 6 may have any suitable size and shape (e.g. conical and tapered conical) to meet the needs and fit the bone structure of the patient. The interior of the body of implant casing 6 is also threaded for a reason that will soon be disclosed.

Rows of vertically aligned pin holes 8 are spaced around the threaded body of implant casing 6. The pin holes 8 are sized to slidably receive hollow locking pins 10 having sharp tips that are adapted to bore into the patient's bone structure and thereby anchor the implant casing 6. The locking pins 10 are manufactured from titanium, titanium alloy or hydroxy apatite ceramic which are all known to integrate with bone. Each locking pin 10 has one or more open window or grooves 12 formed therein for a purpose that will soon be described.

Initially, the pins 10 are retracted within the hollow body of the implant casing 6 during implantation. However, as will be described when referring to FIGS. 4 and 5, once the implant casing 6 is suitably positioned and anchored in the patient's bone structure, the locking pins 10 can be forced outwardly from the casing via respective ones of the pin holes 8 and into engagement with the bone structure. At this point, an enzyme containing a human bone tissue growth factor may be expulsed from the hollow body of the implant casing 6 by way of the windows 12 formed in the locking pins 10.

A relatively wide and hollow implant head 14 surrounds the cylindrical body of the implant casing 6. A plurality of (e.g. four) locking grooves 16 are uniformly spaced around the implant head 14. The implant head 14 has a bowl-shaped entry port 15 that tapers inwardly towards the hollow body of implant casing 6 so as to be able to accommodate a matching portion from and provide a machine tapered seal with a pin activator 18, as will now be described.

The root portion 2 of the implant bone locking mechanism and artificial periodontal ligament system 1 also includes the pin activator 18 that is preferably manufactured from the same type of (e.g. titanium based) metal as is the implant casing 6 so as to prevent corrosion galvanic reactions. The pin activator 18 has an elongated abutment stem 20 that terminates with a round point. The abutment stem 20 is sized to be received inwardly through the hollow body of the implant casing 6 so as to activate (expel) the locking pins 10 through pin holes 8. In this regard, the exterior of the abutment stem 20 is provided with external screw threads that correspond with the internal screw threads of implant casing 6, whereby the abutment stem 20 can be rotated into mating engagement with the implant casing 6 at the hollow interior thereof.

A relatively wide and hollow abutment head 22 having a series of internal screw threads 23 extending therearound is coextensively joined to the abutment stem 20 by means of a neck 24. The neck 24 is machined so as to have an inwardly tapered shape that matches the shape of the entry port 15 within the implant head 14 of implant casing 6 so that a close sealing fit is established therebetween when the abutment stem 20 of pin activator 18 is rotated into mating engagement with the implant casing 6.

A plurality of (e.g. four) locking grooves 26 are uniformly spaced around the abutment head 22 of pin activator 18 to correspond with the locations of the locking grooves 16 that are formed in the implant head 14 of implant casing 6. Therefore, when the abutment stem 20 of pin activator 18 is rotated into mating engagement with the implant casing 6, the locking grooves 26 of the abutment head 22 of pin activator 18 will be located above and axially aligned with the locking grooves 16 of the implant head 14 of implant casing 6.

A swivel pocket 28 is formed at the bottom of the hollow abutment head 22 of the pin activator 18. An elastomeric material (designated 104 in FIGS. 6 and 7) fills the swivel pocket 28 of abutment head 22 in order to provide a cushion for a ball swivel of a swivel rod 40 of the crown portion 4 as will soon be disclosed. The elastomeric material 104 is preferably manufactured from a non-allergenic biocompatible pure grade silicon rubber.

The crown portion 4 of the implant bone locking mechanism and artificial periodontal ligament system 1 is coupled to the previously described root portion 2. The crown portion 4 includes a locking basket 30 that is preferably manufactured from the same (e.g. titanium) metallic material or alloy as are the implant casing 6 and the pin activator 18 of the root portion 2 so that the patient's gum will bond by means of epithelial attachment to the locking basket. The locking basket 30 has a pair of scoopshaped wings 32 projecting outwardly and in opposite directions relative to one another. The opposing wings 32 surround and define a central opening 34 of the locking basket. A resilient material (designated 106 in FIGS. 6 and 7) covers the top of the wings 32 to provide a cushion surface for a crown that is to be seated upon the scoop-shaped wings 32 of locking basket 30.

A plurality of (e.g. four) parallel aligned locking splines 36 project downwardly from the bottom of the wings 32 of locking basket 30. The locking splines 36 are surrounded by and encased in a cylindrical skirt 38. The locking spines 36 are spaced from one another so as to lie below and surround the central opening 34 of the locking basket 30. In the assembled configuration of FIGS. 6 and 7, the locking splines 36 extend through respective ones of the axially aligned locking grooves 26 and 16 of the pin activator 18 and the implant casing 6. Accordingly, the locking basket 30 will sit atop the abutment head 22 of pin activator 18 with the central opening 34 of the locking basket 30 positioned above and axially aligned with the swivel pocket 28 formed in the abutment head 22.

The crown portion 4 also has a swivel rod 40. A series of adjustment grooves 42 extend around the top end of swivel rod 40, and a relatively large ball swivel 44 is formed at the bottom end of the swivel rod 40. In the assembled configuration of FIGS. 6 and 7, the swivel rod 40 extends in coaxial alignment through the central opening 34 of the locking basket 30 so as to be received at and adapted for pivotal movement within the swivel pocket 28 in the abutment head 22 of the pin activator 18.

A short, cylindrical swivel nut 46 having a hollow interior surrounds the swivel rod 40 between the adjustment grooves 42 and the ball swivel 44 at opposite ends thereof. A plurality of (e.g. four) assembly notches 48 are formed in and spaced at equal distances around the swivel nut 46. A series of external screw threads 50 extend around the swivel nut 46 below the assembly notches 48. In the assembled configuration of FIGS. 6 and 7, the external screw threads 50 of swivel nut 46 are mated to the internal screw threads 23 of the abutment head 22 of the pin activator 18.

What is more, the bottom of the swivel nut 46 is provided with an internal ball socket 52 which is beveled and extends around the periphery of nut 46. When the swivel nut 46 and the abutment head 22 of pin activator 18 are mated together at the respective sets of screw threads 50 and 23, the beveled ball socket 52 of swivel nut 46 surrounds and captures the ball swivel 44 of swivel rod 40 so that the ball swivel 44 will be received and retained between the swivel pocket 28 and swivel nut 46. It may now be appreciated that the ball swivel 44 of swivel rod 40 is adapted to pivot within the enclosure formed by the aforementioned swivel pocket 28 and ball socket 52 in response to a rotational force that is applied to the swivel rod 40.

A hemispherically shaped swivel rod connector 54 has a central hole 56 extending therethrough and a depression 57 recessed in the top. In the assembled configuration of FIGS. 6 and 7, the swivel rod 40 is received through the central hole 56 in the swivel rod connector 54 so that swivel rod connector 54 surrounds the swivel rod 40 below the adjustment grooves 42 thereof. With swivel rod connector 54 properly seated at the bottom of a tapered cavity 102 that runs longitudinally through the crown 100, the crown 100 will be able to slide along the outer surface of the hemispherical swivel rod connector 54.

Figure 6:
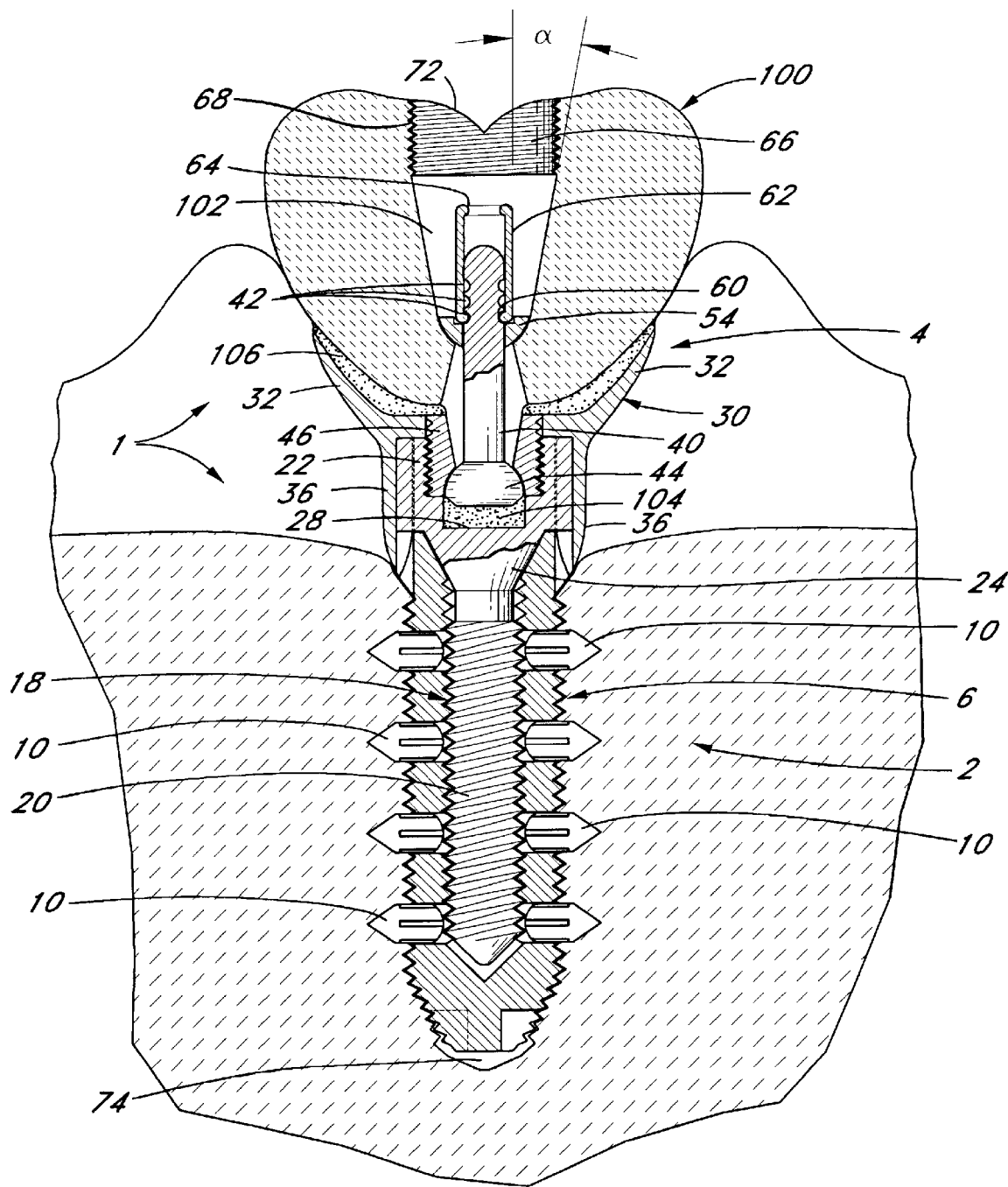

As is best shown in FIGS. 6 and 7, a flexible metal or plastic locking tube 62 surrounds the adjustment grooves 42 at the top end of swivel rod 40. Located at the bottom and extending around the interior of locking tube 62 is a snap ring 60. The snap ring 60 is selectively positioned in one of the adjustment grooves 42 of swivel rod 40, and the flexible locking tube 62 surrounds and hold snap ring 60 in compression therewithin.

The locking tube 62 has a longitudinal slit 63 (best shown in FIG. 1) by which to enable tube 62 to flex during the positioning of snap ring 60 within one of the adjustment grooves 42. To this end, located at the top and extending around the interior of locking tube 62 is an identical snap ring 64 that is sized to be engaged by a suitable tool (not shown) so that locking tube 62 can be removed from swivel rod 40 when it is necessary or desirable to adjust the position of snap ring 60 relative to the adjustment grooves 42. In this regard, it may be appreciated that locking tube 62 is reversible so that the functions of snap rings 60 and 64 are interchangeable.

In the assembled relationship, with the combination snap ring 60 and locking tube 62 located in surrounding engagement with the swivel rod 40, the locking tube 62 is seated upon the swivel rod connector 54 and received within the depression 57 at the top thereof in order to maintain tube 62 in a state of compression so that snap ring 60 will be reliably retained within the preselected one of the adjustment grooves 42.

The crown portion 4 of system 1 is completed by closing the the cavity 102 through crown 100 by means of a plug member 66 which functions as a seal against oral fluids. Plug member 66 is preferably manufactured from a composite (e.g. acrylic) material and includes a disk-like body having a set of external screw threads 68 extending therearound. A suitably shaped (e.g. phillips or hexagonal) recess 72 is formed in the top of plug member 66 to receive therewithin a wrench, or similar tool, so that the plug member 66 may be tightened down or removed from the crown 100.

Figure 2:
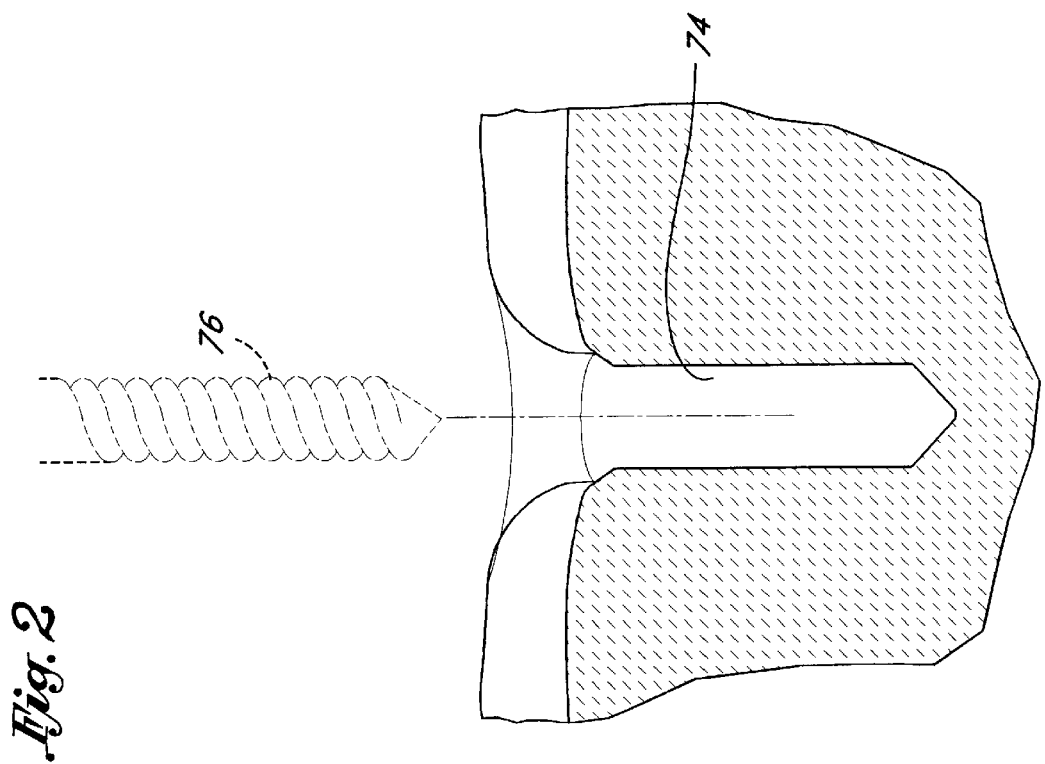

FIGS. 2–5 of the drawings illustrate the steps of implanting and installing the implant bone locking mechanism and artificial periodontal ligament system 1 of this invention. In FIG. 2, a portion of the patient's gum tissue is removed and a hole 74 is drilled through the bone structure. By way of example, the hole 74 can be formed with any conventional drill bit 76 that is used in dentistry for the installation of dental implants.

Figure 3:
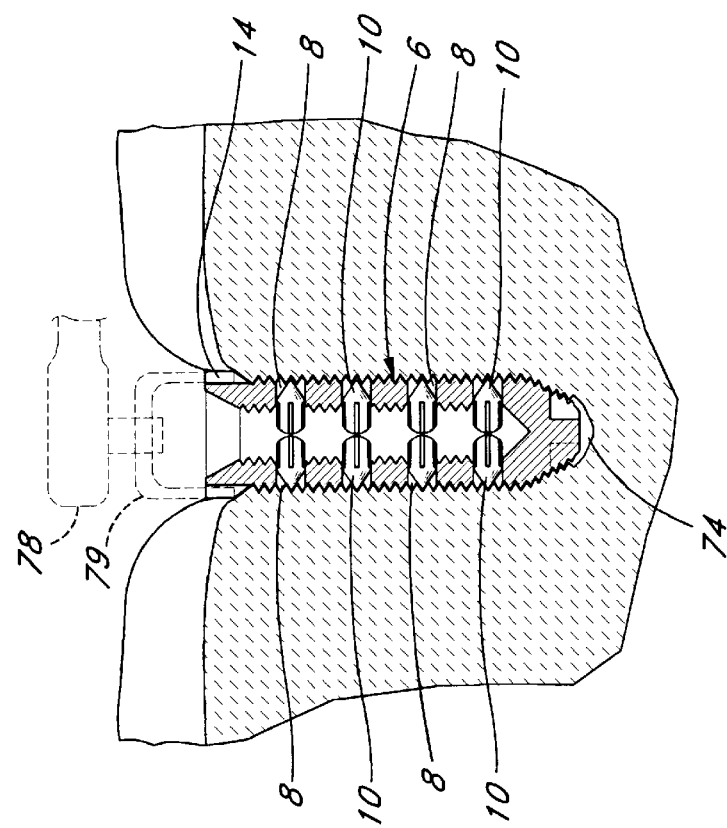
FIGS. 2–5 show the steps by which the implant bone locking mechanism and artificial periodontal ligament system of FIG. 1 is implanted and assembled within a hole that is drilled in the patient's bone.

In FIG. 3, a commercially available dental hand piece 78 and a suitably sized socket 79, such as those manufactured by SteriOss Company of Yorba Linda, California are used to grasp the locking grooves (designated 16 in FIG. 1) of the implant head 14 in order to rotate the implant casing 6 of the system 1 into the hole 74 that has been drilled through the patient's bone structure. During installation of the implant casing 6, the locking pins 10 are initially located inwardly through respective pin holes 8 so as not to impede the insertion of implant casing 6 into the hole 74.

Once the implant casing 6 is installed, the external screw threads thereof bite into the surrounding bone structure to avoid an inadvertent removal of casing 6 from hole 74. The implant head 14 of implant casing 6 is disposed at the top of hole 74 for receipt of the pin activator 18 (in the manner shown in FIG. 4). Lastly, a tissue growth factor, such as bone morphogenic proteins, platelet derived growth factors, insulin derived growth factors, or the like, is injected into the hollow interior of the implant casing 6 to be delivered to the surrounding bone structure for the purpose of decreasing the bone to implant integration time.

Figure 4:
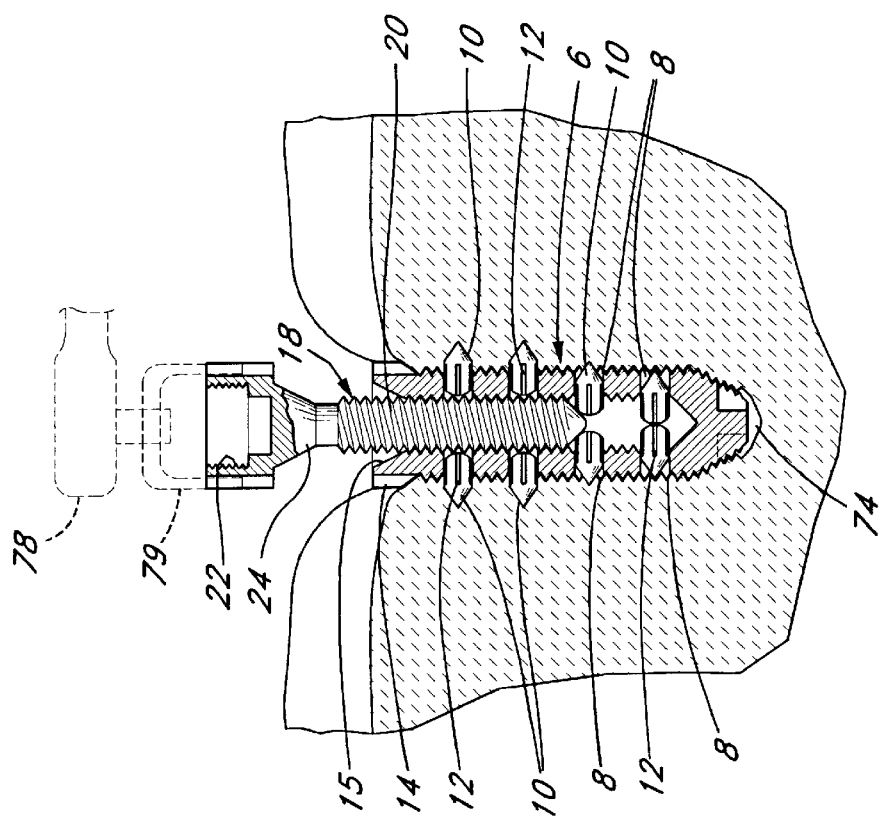

In FIG. 4, the aforementioned dental hand piece 78 and the same or a different socket 79 are now used to grasp the locking grooves (designated 26 in FIG. 1) of the abutment head 22 in order to rotate the pin activator 18 through the interior of the implant casing 6 so that the external screw threads of the abutment stem 20 of pin activator 18 are mated to the corresponding internal screw threads of the implant casing 6. During assembly of the pin activator 18 into implant casing 6, the axially advancing abutment stem 20 drives the locking pins 10 outwardly through respective ones of the pin holes 8. At the same time, the axially advancing abutment stem 20 of pin activator 18 also compresses the tissue growth factor at the interior of implant casing 6 so that the growth factor is expulsed outwardly from and uniformly distributed along the casing 6 via the windows 12 that are formed through locking pins 10.

Figure 5:
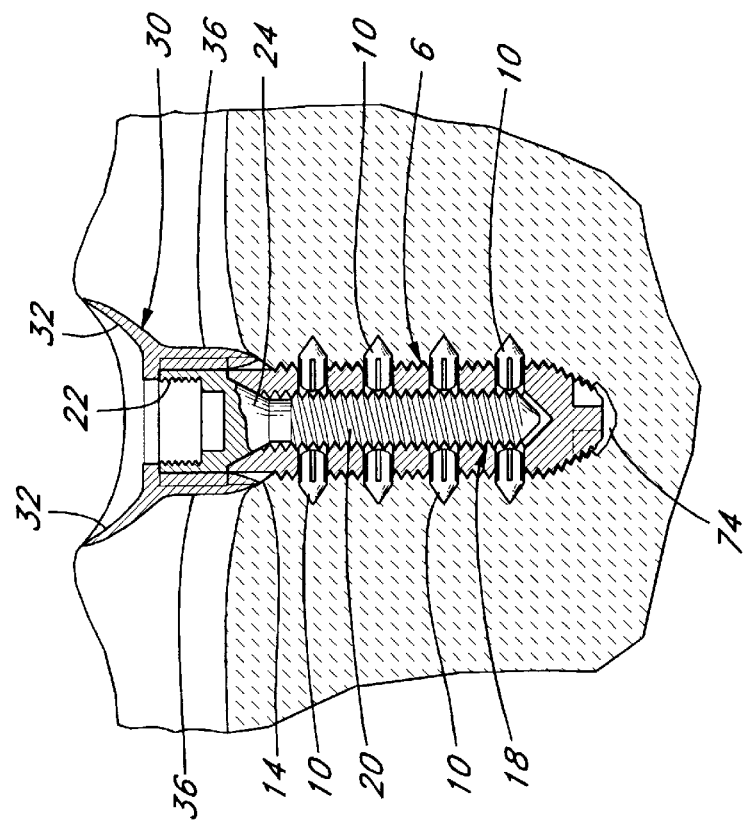

In FIG. 5, the pin activator 18 is shown completely installed within the implant casing 6. Accordingly, the locking pins 10 are fully extended so that the sharp tips thereof bore into the surrounding bone structure to anchor the root portion (designated 2 in FIG. 1) of the system 1 within the hole 74. The locking pins 10 stabilize and lock the implant casing 6 to the bone structure to prevent micromovement and thereby avoid a primary cause of implant failure and possible damage to the surrounding bone structure. Moreover, the tapered neck 24 of the pin activator 18 is press fit against and seated upon the opposing bowl shaped entry port 15 at the implant head 14 of implant casing 6 to form a tight fluid seal therebetween and prevent contamination.

With the root portion 2 fully installed, the locking basket 30 is coupled to the implant casing 6 and pin activator 18 as earlier described. That is, the locking splines 36 of locking basket 30 which extend downwardly from the outwardly stretched wings 32 are received through respective axially aligned locking grooves (designated 16 and 26 in FIG. 1) of the implant head 14 of implant casing 6 and the abutment head 22 of pin activator 18. The locking splines 36 interconnect the implant head 14 with the abutment head 22 so that one cannot rotate relative to the other. What is more, the patient's epithelial gum tissue can attach and grow around the wings 32 and the cylindrical skirt 38 of the locking basket 30.

After the locking basket 30 is installed, the crown (designated 100 in FIGS. 6 and 7) is affixed to the assembly so as to lie above the patient's gum line and be capable of moving up and down and sliding laterally along the wings 32 of locking basket 30. The crown 100 is manufactured from a conventional crown material, such as porcelain, porcelain fused to metal, dental acrylic, gold, silver, and the like.

Turning now to FIGS. 6 and 7 of the drawings, the root and crown portions 2 and 4 of the implant bone locking mechanism and artificial periodontal ligament system 1 are shown as assembled within the hole 74 and firmly anchored to the patient's bone structure which surrounds hole 74. The crown 100 is seated upon the locking basket 30 with the resilient material 106 disposed between the crown 100 and the outstretched wings 32 of locking basket 30. The crown 100 is shown irremovably connected to the system 1 by means of the swivel rod 40 which permits the crown to slide along the wings 32 of the basket 30.

More particularly, and as previously disclosed, the bottom end of connecting rod 40 terminates at the ball swivel 44. Ball swivel 44 is enclosed by the swivel nut 46 and abutment head 22 of the pin activator 18. In this regard, the ball swivel 44 is received in the swivel pocket 28 of the abutment head 22 and seated upon the elastomeric material 104 therewithin. By virtue of the foregoing, and as an important feature of this invention, the ball swivel 44 acts as a first pivot point, whereby the swivel rod is adapted to rotate. In addition, the elastomeric material 104 within swivel pocket 28 absorbs and dissipates the compressive loads that are applied from the crown 100 to the ball swivel 44 via swivel rod 40 so as to cause the ball swivel 44 to be momentarily pushed downwardly into the swivel pocket 28. The resilient, springlike nature of the resilient material 104 pushes the ball swivel 44 upwardly from the swivel pocket 28 when the compressive load is removed from crown 100.

As was also previously disclosed, the top end of the swivel rod 40 is supported within the cavity 102 through crown 100 by the hemispherically shaped swivel rod connector 54. The swivel rod connector 54 also holds the crown 100 atop the locking basket 30. The crown 100 may be held against locking basket 30 with varying degrees of tightness, depending upon the particular adjustment groove 42 of swivel rod 40 within which snap ring 60 of locking tube 62 is located and the corresponding compressive force that is applied to the resilient material 106. The position of the snap ring 60 can be changed by pushing downwardly on the locking tube 62 to force snap ring 60 to jump from one adjustment groove 42 to the next.

As another important feature of this invention, the swivel rod connector 54 acts as a second pivot point, whereby the crown 100 can slide along the wings 32 of locking basket 30 through an angle designated a in FIG. 6. Thus, it may be appreciated that the implant bone locking mechanism and artificial periodontal ligament system 1 is characterized by dual pivot points (i.e. ball swivel 44 and swivel rod connector 54) that are carried at opposite ends of the swivel rod 40.

Accordingly, the crown 100 is adapted to move relative to the locking basket 30 in two perpendicularly aligned directions. That is to say, the crown 100 is capable of riding from side-to-side over the outstretched wings 32 of basket 30 and (because of the spring-like nature of the resilient materials 104 and 106) towards and away from the swivel pocket 28 of the abutment head 22 of the pin activator 18.

In this same regard, the degree of movement of the crown 100 can be selectively controlled depending upon the thickness and type of resilient material, the location of snap ring 60 in one of the adjustment grooves 42 of swivel rod 40, and the dimensions of the locking basket 30. By virtue of the foregoing, the crown 100 will closely emulate the movement of a natural tooth so as to minimize patient discomfort, prolong the life and function of the crown, increase the quality of mastication, and reduce the chance of damage to the bone structure to which the crown is affixed.

It will be apparent that while a preferred embodiment of the invention has been shown and described, various modifications and changes may be made without departing from the true spirit and scope of the invention. For example, it is to be understood that the implant bone locking mechanism and artificial periodontal ligament system of this invention has application with single crowns, as illustrated in the drawings, or with bridge abutments, partial denture attachments, complete dentures, and other uses where an implant must remain immobile, but when it is desireable to have a dental appliance or prosthetic device move relative thereto.

Having thus set for the preferred embodiment, what is claimed is:

1. A dental implant system for affixing a crown to the bone structure within a patient's mouth, said dental implant system comprising:

a root portion to be located substantially below the patient's gum line in a hole made in the patient's bone structure;

means by which to anchor the root portion to the bone structure within which the hole is made;

a crown portion located above said root portion, the crown being irremovably connected to said crown portion;

means by which to couple said crown portion to said root portion; and means by which to permit the crown to move laterally, upwardly and downwardly relative to said crown portion so as to emulate the movement of a natural tooth.

2. The dental implant system recited in claim 1, wherein said root portion includes a hollow implant casing to be received within the hole made in the patient's bone structure, said means by which to anchor said root portion to the bone structure including a plurality of locking pins located within said hollow implant casing and movable outwardly therefrom to bore into the bone structure surrounding said implant casing.

3. The dental implant system recited in claim 2, wherein said means by which to anchor said root portion to the bone structure also includes a set of threads at the exterior of said hollow implant casing to bite into the bone structure surrounding said implant casing when said implant casing is received within the hole made in the bone structure.

4. The dental implant system recited in claim 2, further comprising a supply of bone tissue growth factor located within said hollow implant casing to be expulsed therefrom after said implant casing is received within the hole made in the bone structure to promote the growth of bone tissue around said implant casing.

5. The dental implant system recited in claim 4, wherein said plurality of locking pins have open windows formed therein, said bone tissue growth factor being expulsed from said hollow implant casing via said open windows when said locking pins are moved outwardly of said implant casing to bore into the bone structure surrounding said implant casing.

6. The dental implant system recited in claim 2, wherein said root portion also includes a pin activator having a elongated abutment stem, said abutment stem moving axially through said hollow implant casing to force said plurality of locking pins to move outwardly of said implant casing to bite into the bone structure surrounding said implant casing.

7. The dental implant system recited in claim 6, wherein said crown portion includes a locking basket having a pair of outstretched wings upon which the crown is seated, said means by which to couple said crown portion to said root portion including a plurality of locking splines extending from said locking basket to engage said hollow implant casing and said pin activator to prevent the rotation of said implant casing and said pin activator relative to said locking basket and to one another.

8. The dental implant system recited in claim 6, wherein said crown portion also includes a swivel rod, a first end of said swivel rod connected to the crown and the opposite end of said swivel rod connected to said root portion, said means by which to permit the crown to move relative to said crown portion comprising a first pivot surface located at said opposite end of said swivel rod and pivotally connected to said root portion to permit said swivel rod to rotate and the crown to slide laterally along the outstretched wings of said locking basket.

9. The dental implant system recited in claim 8, wherein said first pivot surface of said swivel rod is a ball that is pivotally connected to said root portion at a swivel pocket formed in said pin activator, said root portion also including elastomeric material having a spring memory located within said swivel pocket to support said ball so that said ball is capable of moving towards and away from said swivel pocket, whereby the crown is adapted to move upwardly and downwardly relative to said locking basket in response to a compressive force applied to the crown, said compressive force transmitted from the crown to said ball via said swivel rod.

10. The dental implant recited in claim 9, wherein said crown portion also includes resilient material having a spring memory and covering the outstretched wings of said locking basket to support the crown, the compressive force applied to the crown being transmitted to said resilient material when the crown moves downwardly relative to said locking basket.

11. The dental implant recited in claim 8, wherein said means by which to permit the crown to move relative to said crown portion further comprises a second pivot surface located at the first end of said swivel rod and pivotally connected to the crown.

12. The dental implant recited in claim 11, wherein said second pivot surface is a hemispherically shaped swivel rod connector surrounding the first end of said swivel rod, the crown being adapted to rotate around said hemispherically shaped swivel rod connector and slide laterally along the outstretched wings of said locking basket.

13. The dental implant recited in claim 12, wherein said crown portion also includes a snap ring surrounding the first end of said swivel rod and being seated upon said swivel rod connector to hold said swivel rod connector in mating engagement against the crown.

14. The dental implant system recited in claim 13, wherein said crown portion also including a locking tube surrounding said snap ring and holding said snap ring in compression around the first end of said swivel rod and seated upon said swivel rod connector, an axial pushing force applied to said locking tube being transferred to said snap ring to cause said snap ring to move axially along said swivel rod and towards said swivel rod connector to thereby apply a compressive force to said swivel rod connector.

15. A dental implant system for affixing a crown to the bone structure within a patient's mouth, said dental implant system comprising:
a root portion to be located substantially below the patient's gum line in a hole made in the patient's bone structure;
means by which to anchor said root portion to the bone structure in which the hole is made;
a crown portion coupled to said root portion, said crown portion including a locking basket having a pair of outstretched wings and a plurality of locking splines depending therefrom to engage said root portion and thereby prevent said root portion from rotating relative to said crown portion;
means by which to irremovably connect the crown to said crown portion so that the crown is seated upon said locking basket and adapted to slide in a first direction laterally along the outstretched wings of said locking basket and in a second direction up and down relative to said locking basket, said first and second directions lying in substantially perpendicular alignment with one another.

16. A dental implant system for affixing a crown to the bone structure within a patient's mouth, said dental implant system comprising:
a root portion to be located substantially below the patient's gum line in a hole made in the patient's bone structure, said root portion including a hollow implant casing to be received within said hole, a supply of bone tissue growth factor located within said hollow implant casing, and openings formed through said hollow implant casing through which said bone tissue growth factor is expulsed after said hollow implant casing is received within said hole so as to promote the growth of bone tissue around said hollow implant casing;

means by which to anchor the hollow implant casing of said root portion to the bone structure within which the hole is made;

a crown portion located above said root portion, the crown being irremovably connected to said crown portion;

means by which to couple said crown portion to said root portion; and means by which to permit the crown to move relative to said crown portion so as to emulate the movement of a natural tooth.

17. The dental implant system recited in claim 16, wherein said means by which to anchor said hollow implant casing of said root portion to the bone structure includes a set of threads at the exterior of said hollow implant casing to bite into the bone structure surrounding said implant casing when said implant casing is received within the hole made in the bone structure.

18. The dental implant system recited in claim 16, wherein said means by which to anchor said hollow implant casing of said root portion to the bone structure includes a plurality of locking pins, each of said plurality of locking pins located within said hollow implant casing and movable outwardly therefrom via respective ones of said openings formed through said hollow implant casing to bore into the bone structure surrounding said implant casing.

19. The dental implant system recited in claim 18, wherein said plurality of locking pins have open windows formed therein, said bone tissue growth factor being expulsed from said hollow implant casing through said open windows of said locking pins when said locking pins are moved outwardly of said implant casing to bore into the bone structure surrounding said implant casing.

20. The dental implant system recited in claim 19, wherein said root portion also includes a pin activator having an elongated abutment stem, said abutment stem moving axially through said hollow implant casing to force said plurality of locking pins to move outwardly of said hollow implant casing via said respective openings formed through said implant casing to bite into the bone structure surrounding said implant casing.

\* \* \* \* \*